United States Patent

Molteni et al.

[11] 4,048,305
[45] Sept. 13, 1977

[54] TRIPEPTIDES, THEIR ESTERS AND AMIDES, AND ANTI-ULCERA ACTIVITY THEREOF

[75] Inventors: Luigi Molteni, Malnate, Varese; Gian Piero Vercesi, Rho, Milan; Eraldo Antonini, Rome, all of Italy

[73] Assignee: Dr. L. Zambeletti S.p.A., Milan, Italy

[21] Appl. No.: 674,947

[22] Filed: Apr. 8, 1976

[30] Foreign Application Priority Data

Apr. 9, 1975 Italy .................................. 22190/75

[51] Int. Cl.² ............................................. A61K 37/00
[52] U.S. Cl. ............................. 424/177; 260/112.5 R
[58] Field of Search ................... 260/112.5 R; 424/177

[56] References Cited

U.S. PATENT DOCUMENTS 3,971,736  7/1976  Wagner et al. ............... 260/112.5 R Primary Examiner—Delbert R. Phillips Attorney, Agent, or Firm—Dennis P. Clarke

[57] ABSTRACT

This invention relates to a series of tripeptides of the general formula:

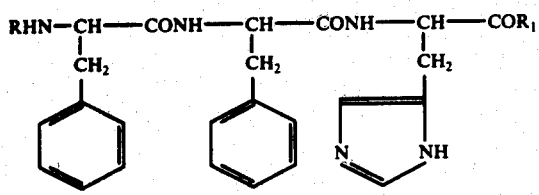

wherein
R = — H, $COCH_3$, alkyl
$R_1$ = —OH, —$NH_2$, —NH alkyl ($C_1$-$C_5$) —O alkyl ($C_1$-$C_5$)

resulting from condensing of racemic, levorotatory and dextrorotatory phenylalanine and histidine and having an anti-ulcer activity.

9 Claims, No Drawings

TRIPEPTIDES, THEIR ESTERS AND AMIDES, AND ANTI-ULCERA ACTIVITY THEREOF

This invention relates to a series of tripeptides of the general formula:

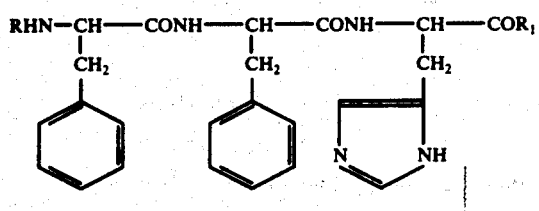

wherein
R = — H, COCH$_3$, alkyl
R$_1$ = —OH, —NH$_2$, —NH alkyl (C$_1$–C$_5$) —O alkyl (C$_1$–C$_5$)
resulting from condensing of racemic, levorotatory and dextrorotatory phenylalanine and histidine This invention further relates to the salts of the compounds of the general formula (1) which are physiologically acceptable (hydrochlorides, sulphates, succinates, maleates, etc.); and further pharmaceutical compositions with anti-gastric and anti-ulcer activity containing as an active element one of the compounds of formula (1).

A further object of the invention is a procedure for preparing the above-mentioned compounds.

According to such procedure, the preparation process occurs following a scheme which may be represented as below:

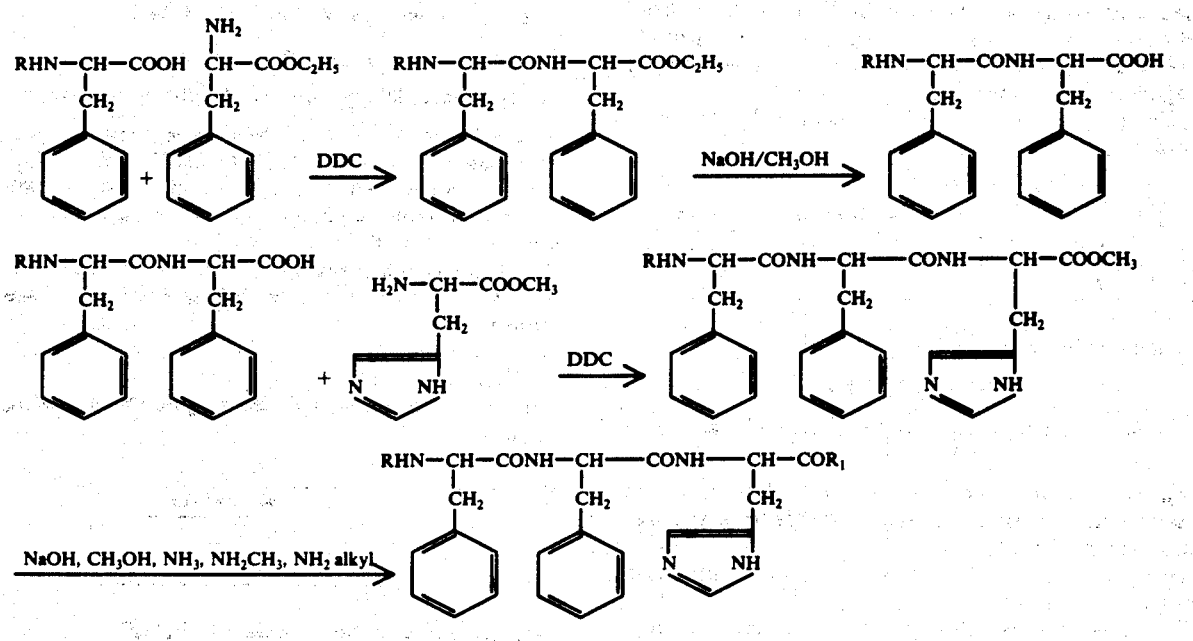

The following examples illustrate but do not limit the above described procedure:

EXAMPLE I

N-acetyl-l-phenylalanyl-l-phenylalanine ethylester g. 46 of l-phenylalanine ethylester (freshly prepared by neutralizing the corresponding hydrochloride with a saturated solution of potassium carbonate) are dissolved into 500 ml of anhydrous methylene chloride.

To this solution g. 52 of dicyclohexylcarbodiimide dissolved into 150 ml of methylene chloride are added under stirring, and, after cooling, 49.5 g. of N-acetylphenylalanine at one blow are added; then the mixture is left under stirring at room temperature for 48 hours. 2.5 ml of acetic acid are added, and the precipitate of dicyclohexylurea is filtered off. The methylene chloride solution is concentrated, cooled and again filtered. Afterwards, the methylene chloride solution is extracted twice with 1 N HCl, twice with H$_2$O, twice with 1N potassium bicarbonate and finally with distilled H$_2$O to neutrality.

The solution is dried over anhydrous sodium sulphate and concentrated to dryness at a low temperature. By triturating in petroleum ether the solid residue, g. 82 of product are obtained.

m.p. = 142°–145° C [α]$_D^{20}$ = −5 (1% ethanol).

The percent analysis of C, H, N showed the following values:

|  | calculated for | found |
|---|---|---|
| C % | 69.10 | 68.95 |
| H % | 6.90 | 6.70 |
| N % | 7.30 | 7.32 | in accordance with the formula: C$_{22}$H$_{26}$O$_4$N$_2$

EXAMPLE II

N-acetyl-l-phenylalanyl-l-phenylalanine g. 82 of l-phenylalanine ethylester are suspended into 422 ml of methanol and 27 ml of 1N NaOH are added. The temperature spontaneously rises to about 30° C and the mixture is left under stirring at room temperature 1 hour.

At reduced pressure as much as possible methanol is removed, 500 ml of distilled H$_2$O are added, and it is filtered.

The solution is acidified under stirring with concentrated acetic acid and left standing for several hours; then it is filtered and the precipitate is washed several times with ice H$_2$O.

The product after drying weighs g. 74.

m.p. = 240° C [α]$_D^{20}$ = = 1.75 (1% in pyridine).

The percent analysis of C, H, N, gave the following results:

|     | calculated for | found |
|-----|----------------|-------|
| C % | 67.78          | 67.34 |
| H % | 6.26           | 6.41  |
| N % | 7.91           | 7.68  | in accordance with the formula: $C_{20}H_{22}O_4N_2$

EXAMPLE III

N-acetyl-l-phenylalanyl-l-phenylalanyl-l-histidine methylester g. 74 of N-acetyl-l-phenylalanyl-l-phenylalanine are dissolved, under stirring, into 1.3 l of anhydrous piridine at 40° C. g. 35.32 of l-histidine methylester (freshly prepared from the respective hydrochloride) dissolved into 150 ml of anhydrous pyridine and 45.23 g. of dicyclohexylcarbodiimide dissolved into 150 ml of anhydrous pyridine contemporaneously are added. The mixture is hold under stirring at 40° C 24 hours. 2 ml of concentrated acetic acid are added, it is cooled to − 10° C and the precipitate of dicyclohexylurea is filtered off.

The solution is evaporated at reduced pressure at a temperature not higher than 30° C. By successive triturations of the residue in petroleum ether a solid is obtained which is suspended into 400 ml of methylene chloride and extracted twice with 400 ml of 1N HCl.

The hydrochloric extracts collected after removing the traces of methylene chloride, are filtered with charcoal and basified with a saturated solution of potassium carbonate. The precipitate which forms is washed to neutrality with distilled cold H$_2$O. It is crystallized from H$_2$O/methanol and, after drying, g. 19.0 of tripeptide are obtained. m.p. = 160°-165° C (with decomposition) [α]$_D^{20}$ = 12 (1% methanol).

The percent analysis of C, H, N, gave the following results:

|     | calculated for | found |
|-----|----------------|-------|
| C % | 64.14          | 64.37 |
| H % | 6.18           | 6.06  |
| N % | 13.85          | 13.71 | in accordance with the formula: $C_{27}H_{31}O_5N_5$.

EXAMPLE IV

N-acetyl-l-phenylalanyl-l-phenylalanyl-l-histidine methylester g. 21.79 of l-histidine methylester dihydrochloride are suspended into 100 cc. of anhydrous methylene chloride; under stirring at room temperature, 20.82 ml of triethylan mine are added and the mixture is kept under stirring for ½ hour.

g. 18.57 of dicyclohexylcarbodiimide, dissolved into 100 cc. of anhydrous methylene chloride and g. 21.79 of N-acetyl-l-phenylalanyl-l-phenylalanine contemporaneously are added. The mixture is cooled, filtered and the solid mass is extracted with 1N HCl. The methylene chloride phase is extracted with 1N HCl. The hydrochloric phases collected are basified with a saturated solution of potassium carbonate. The pasty mass which forms is washed several times with H$_2$O and then made solid by mixing with sulphuric ether. It is crystallized from methanol/water.

Yield = 20 g. m.p. = 160°-165° C with decomposition [α]$_D^{20}$ = − 12.5 (1% methanol)

The percent analysis of C, H, N gave the following results:

|     | calculated for | found |
|-----|----------------|-------|
| C % | 64.14          | 64.37 |
| H % | 6.18           | 6.00  |
| N % | 13.85          | 13.75 | in accordance with the formula $C_{27}H_{31}O_5N_5$

EXAMPLE V

N-acetyl-l-phenylalanyl-l-phenylalanyl-l-histidine g. 23 of the ester obtained in the examples III and IV are suspended into 230 ml of methanol and, under stirring, 50 ml of 1N sodium hydrate are added. The mixture is left 1h under stirring at room temperature, then is neutralized with 1N HCl.

The precipitate which forms is collected on a filter, washed with cold H$_2$O and, after drying, crystallized from isopropyl alcohol and ether.

g. 6.21 of product are obtained.

m.p. = 143°-145° C with decomposition. [α]$_D^{20}$ = +10 (1% methanol)

The percent analysis of C, H, N, gave the following results:

|     | calculated for | found |
|-----|----------------|-------|
| C % | 63.52          | 63.43 |
| H % | 5.94           | 6.06  |
| N % | 14.24          | 14.32 | in accordance with the formula: $C_{26}H_{29}N_5O_5$

EXAMPLE VI

N-acetyl-l-phenylalanyl-l-phenylalanyl-l-histidineamide

The solution of 20 g of N-acetyl-l-phenylalanyl-l-phenylalanyl-l-histidine methylester in 400 ml of anhydrous methanol, cooled to 0° C, and saturated with anhydrous gaseous ammonia, is kept under stirring at room temperature for 5 days.

The solid which forms is collected on a filter and, after drying, crystallized from H$_2$O. g. 9 of product are obtained.

m.p. = 178°-180° C [α]$_D^{20}$ = − 16.2 (1% CH$_3$COOH)

The percent analysis of C, H, N, gave the following values:

|     | calculated for | found |
|-----|----------------|-------|
| C % | 63.66          | 63.55 |
| H % | 6.16           | 6.17  |
| N % | 17.13          | 16.28 | in accordance with the formula: $C_{26}H_{30}N_6O_4$

EXAMPLE VII

N-acetyl-l-phenylalanyl-l-phenylalanyl-l-histidine methylamide g. 50 of N-acetyl-l-phenylalanyl-l-phenylalanyl-l-histidine methylester are dissolved into 150 ml of absolute methyl alcohol. The solution is cooled to 0° C and is saturated with anhydrous gaseous monomethylamine, at a temperature not higher than 0° C.

At the end of the saturation, the sealed vessel is put under stirring at room temperature for 3 days. The solid which forms is filtered off, washed with ether and dried. g. 7 of product are obtained.

m.p. = 198°-200° C $[\alpha]_D^{20}$ = −16.8 (1% CH₃COOH)

The percent analysis of C, H, N, gave the following values:

|     | calculated for | found |
| --- | --- | --- |
| C % | 64.27 | 64.17 |
| H % | 6.39 | 6.51 |
| N % | 16.65 | 16.45 | in accordance with the formula: $C_{27}H_{32}N_6O_4$

EXAMPLE VIII

N-acetyl-dl-phenylalanyl-dl-phenylalanine ethylester g. 15.8 of dl-phenylalamine ethylester (prepared just at that moment by neutralizing the corresponding hydrochloride with a saturated solution of potassium carbonate) are dissolved into 170 ml of anhydrous tetrathydrofuran.

The solution is cooled outwardly with an ice-bath and 20.18 g. of dicyclohexylcarbodiimide dissolved into 60 ml of anhydrous tetrahydrofuran and 16.94 g. of N-acetyl-dl-phenylalanine are added.

After 1 hour the ice-bath is removed and the mass is stirred at room temperature for 48 hours. 1 ml of acetic acid is added and the mixture is filtered. The solution, after concentrating, is cooled and filtered again. It is dry evaporated taking up several times with methylene chloride to eliminate the tetrahydrofuran.

The solid residue is dissolved into methylene chloride and extracted successively twice with 1N HCl, twice with H₂O, twice with 1N potassium bicarbonate and finally with distilled H₂O to neutrality. The methylene solution is taken to dryness. By triturating repeatedly with sulphuric ether the obtained residue, g. 27 or product are obtained. m.p. = 140°-142° C The percent analysis of C, H, N, gave the following values:

|     | calculated for | found |
| --- | --- | --- |
| C % | 69.10 | 69.22 |
| H % | 6.90 | 6.73 |
| N % | 7.30 | 7.28 | in accordance with the formula: $C_{22}H_{26}O_4N_2$

EXAMPLE IX

N-acetyl-dl-phenylalanyl-dl-phenylalanine g. 27 of the ester described in the Example VIII are suspended into 56 ml of 20% methanolic potash and 14 ml of H₂O are added. The suspension is taken to ebullition for 5', it is cooled, 212 ml of H₂O are added, and it is filtered.

The aqueous solution is acidified with concentrated acetic acid under stirring. The precipitate which forms is collected on a filter, washed with ice-water and dried. After crystallization from absolute etanol, g. 16 of product are obtained.

m.p. = 176°-178° C with decomposition.

The percent analysis of C, H, N, gave the following values:

|     | calculated for | found |
| --- | --- | --- |
| C % | 67.78 | 67.85 |
| H % | 6.26 | 6.40 |
| N % | 7.91 | 7.86 | in accordance with the formula: $C_{20}H_{22}O_4N_2$

EXAMPLE X

N-acetyl-dl-phenylalanyl-dl-phenylalanyl-dl-histidine methylester g. 16 of N-acetyl-dl-phenylalanyl-dl-phenylalanine are dissolved into 280 ml of anhydrous pyridine. At 40° C, and at one shot, g. 9.77 of dicyclohexylcarbodiimide dissolved into 32 ml of acetonitrile and g. 7.63 of dl-histidine methylester dissolved into 32 ml of acetonitrile, are added.

The reaction mass is stirred 24 hours at 40° C. 0.5 ml of acetic acid is added, the mixture is cooled to −10° C and is filtered. The solution is dry evaporated at reduced pressure and at a temperature not higher than 30° C. The residue is taken up several times with methylene chloride to eliminate pyridine as much as possible; then it is dissolved into methylene chloride and is extracted with a saturated solution of potassium bicarbonate and with H₂O to neutrality.

After evaporating the solvent, a residue is obtained which, by trituration with petroleum ether, yields g. 13 of product.

m.p. = 110° C.

The percent analysis of C, H, N, gave the following values:

|     | calculated for | found |
| --- | --- | --- |
| C % | 64.14 | 63.95 |
| H % | 6.18 | 6.15 |
| N % | 13.85 | 13.63 | in accordance with the formula: $C_{27}H_{31}O_5N_5$

EXAMPLE XI

N-acetyl-l-phenylalanyl-d-phenylalanine methylester g. 14.7 of d-phenylalanine ethylester are dissolved into 160 ml of anhydrous tetrahydrofuran.

To this solution, cooled to +5° C, g. 18.5 of dicyclohexylcarbodiimide dissolved into 55 ml of anhydrous tetrahydrofuran and g. 15.76 of N-acetyl-l-phenylalanine under stirring and simultaneously are added. After 1 hour, the cooling bath is removed and the mixture is kept under stirring at room temperature for 48 hours.

3.5 ml of acetic acid are added and after 2 hours the precipitate which is formed is filtered off while washing it with methylene chloride. The solution is dry evaporated at reduced pressure.

The residue is dissolved into methylene chloride and the solution obtained is extracted twice with 1N HCl, twice with H₂O, twice with 1N potassium bicarbonate and finally with distilled H₂O to neutrality. The solution is dried over sodium sulphate and taken to dryness at reduced pressure. By mixing with sulphuric ether, the oily residue is converted to 25.6 g. of solid product.

m.p. = 135°-137° C $[\alpha]_D^{20}$ = +6.8 ± ⅛ (1% ethanol)

The percent analysis of C, H, N, gave the following values:

|     | calculated for | found |
| --- | --- | --- |
| C % | 69.10 | 69.21 |
| H % | 6.90 | 6.72 |
| N % | 7.30 | 7.16 | in accordance with the formula: $C_{22}H_{26}O_4N_2$

EXAMPLE XII

N-acetyl-l-phenylalanyl-d-phenylalanine g. 25 of the ester described in Example XI are suspended into 52 ml of 20% methanolic potash, 13 ml of distilled $H_2O$ are added, and the mixture is taken to ebullition for 5'.

The mixture is cooled, 196 ml of $H_2O$ are added, and it is filtered.

The filtrate is acidifed with concentrated acetic acid. The precipitate is collected on the filter, is washed with freezing $H_2O$ and is dried in a stove under vacuum. It is crystallized from alcohol at 96° C.

Yield = g. 96 m.p. = 202°–205° C $[\alpha]_D^{20} = -17.5$ (1% in pyridine)

The percent analysis of C, H, N, gave the following values:

|     | calculated for | found |
| --- | --- | --- |
| C % | 67.78 | 67.89 |
| H % | 6.26 | 6.42 |
| N % | 7.91 | 7.82 | in accordance with the formula: $C_{20}H_{22}O_4N_2$

EXAMPLE XIII

N-acetyl-l-phenylalanyl-d-phenylalanyl-l-histidine-methylester g. 16 of N-acetyl-l-phenylalanyl-d-phenylalanine are dissolved into 245 ml of anhydrous pyridine while mildly heating to 40° C. To this solution g. 7.63 of l-histidine methylester, dissolved into 44 ml of anhydrous acetonitrile and g. 9.77 of dicyclohexylcarbodiimide dissolved into 44 ml of anhydrous acetonitrile are added.

The mixture is left standing at 40° C under stirring for 1 day. Two hours before the completion of the reaction, 0.5 ml of concentrated acetic acid is added, then it is cooled to −10° C and it is filtered.

The solution is evaporated under vacuum and taken up several times with methylene chloride. The residue is dissolved into methylene chloride and it is extracted twice with $H_2O$, with a sodium bicarbonate saturated solution, and finally with $H_2O$ to neutrality.

The solution is dried over anhydrous sodium sulphate and evaporated to dryness at reduced pressure. The residue is taken up several times with acetone and dry concentrated. The solid obtained is suspended into anhydrous ether and is refluxed for 15'. It is filtered to give g. 10.6 of product.

m.p. = 112°–115° C. $[\alpha]_D^{20} = 6.5 \pm 0.2$ (1% in pyridine)

The percent analysis of C, H, N, gave the following values:

|     | calculated for | found |
| --- | --- | --- |
| C % | 64.14 | 63.83 |
| H % | 6.18 | 7.10 |
| N % | 13.85 | 13.68 | in accordance with the formula: $C_{27}H_{31}N_5O_5$

EXAMPLE XIV

N-acetyl-l-phenylalanyl-l-phenylalanyl-l-histidineamide hydrochloride.

g. 10 of N-acetyl-l-phenylalanyl-l-phenylalanyl-l-histidineamide are warm dissolved into the minimum amount of methanol.

The solution is acified with gaseous hydrochloric acid dissolved into ethyl ether and is dry concentrated under vacuum.

The residue which is obtained is crystallized from n-butyl alcohol and ether to give g. 9.5 of product.

m.p. = 120° C with decomposition. $[\alpha]_D^{20} = 12.2$ (1% in water)

The percent analysis of C, H, N, Cl gave the following values:

|     | calculated for | found |
| --- | --- | --- |
| C % | 59.25 | 59.21 |
| H % | 5.93 | 5.90 |
| N % | 15.95 | 15.93 |
| Cl% | 6.73 | 6.69 | in accordance with the formula: $C_{26}H_{30}N_6O_4 \cdot HCl$

The compounds of the present invention were tested for toxicity and gastro-protective activity. The acute toxicity of all the substances tested was found to be very moderate and, only for some more exemplary compounds, was reported in the enclosed table together with the anti-ulcer activity.

The acute toxicity was assayed in "Swiss" strain male mouse weighing 20–24 g. which were held, before the test, in the cages for 10 days at standard ambient conditions (temperature 22° C, humidity about 50%) and kept on a controlled diet (Altromin).

Before the test, the animals were deprived of food for 15 hours, while leaving water "ad libitum".

Lethality was determined on 10 animals for each group-dose by using on the whole 60 animals for each product. For administration, the products were suspended into peanut oil and administered at the maximum volume of 0.1 ml/10 g. of body weight, by means of a gastric probe.

The acute toxicity of the test products is very slight and, hence, is was impossible to attain, at doses consistent with administration, lethal effects, except for N-acetyl-l-phenylalanyl-l-phenylalanyl-l-histidine, the $LD_{50}$ of which is approximately 5 g./Kg.

Gastro-protective activity of the products was assayed on rats by employing the Shay method (Shay H., Komarov, S. A., Fels, S. S., Meranze, D;, Gruenstein, M. and Siplet, H:Gastroenterology, 5, 43-61, 1945).

The investigation was performed on female rats of "Wistar" strain, of the average weight of 200 g., which had been held, before experiment, in the cages for 10 days at standard ambient conditions (temperature 22° C, humidity about 50%) on a controlled diet (Altromin).

72 hours before the test the animals, distributed into individual cages, were deprived of food while leaving water "ad libitum".

At the end of this time, the animals were anaesthetized with ether and, by opening the abdomen, the tying of the pylorus was effected as well as, thereafter, the administration of the products in the dose of 100 mg/Kg dissolved into peanut oil. The suture of the abdomen was then performed and the animals were then placed again into their respective contention cages.

For each product 15 animals were used whilst another set of 15 animals, which served as control, was given peanut oil at the same volume as that of the treated ones.

After 18 hours from administration of the products, the animals were killed under chloroformic narcosis, the stomachs were removed and opened along the greter curvature and then fixed on cork supports for counting the number of ulcers present in the "rumen" and for evaluating the depth of the lesions by arbitrarily assigning values ranging from 1 to 4 according to the intensity of the lesion.

All the assayed substances showed to possess a gastro-protective activity, associated with a very low toxicity. The substances which were found to be the most interesting from a pharmacologic point of view and such that a clinical employment thereof can be expected, are: N-acetyl-l-phenylalanyl-d-phenylalanyl-l-histidine methylester; N-acetyl-l-phenylalanyl-d-phenylalanyl-l-histidineamide; N-acetyl-dl-phenylalanyl-dl-phenylalanyl-dl-histidine methylester; N-acetyl-l-phenylalanyl-l-phenylalanyl-l-histidine methylester; N-acetyl-l-phenylalanyl-l-phenylalanyl-l-histidineamide; N-acetyl-l-phenylalanyl-l-phenylalanyl-l-histidine and N-acetyl-l-phenylalanyl-l-phenylalanyl-l-histidyl-methylamide.

TABLE

| Compounds | Mouse LD$_{50}$:mg/Kg/os | Rat (Shay test) | |
|---|---|---|---|
| | | No. of ulcers M ± es | Ulcer depth M ± es |
| Peanut oil (controls) | — | 10.7 ± 2.2 | 2.4 ± 0.5 |
| N-acetyl-p-phenylalanyl-d-phenylalanyl-p-histidine methylester | > 5000 | 5.6 ± 1.5 | 1.5 ± 0.4 |
| N-acetyl-p-phenylalanyl-d-phenylalanyl-p-histidineamide | > 5000 | 6.2 ± 1.6 | 1.3 ± 0.2 |
| N-acetyl-dl-phenylalanyl-dl-phenylalanyl-dl-histidine methylester | > 5000 | 6.7 ± 1.7 | 1.7 ± 0.2 |
| N-acetyl-p-phenylalanyl-p-phenylalanyl-p-histidine methylester | > 5000 | 4.6 ± 1.1 | 1.1 ± 0.3 |
| N-acetyl-p-phenylalanyl-p-phenylalanyl-p-histidineamide | > 5000 | 3.1 ± 1.7 | 1.1 ± 0.4 |
| N-acetyl-p-phenylalanyl-p-phenylalanyl-p-histidine | ≅ 5000 | 8.4 ± 1.8 | 2.1 ± 0.3 |
| N-acetyl-p-phenylalanyl-p-phenylalanyl-p-histidyl-methylamide | > 5000 | 5.8 ± 1.4 | 1.4 ± 0.3 |

The substances which are the object of the invention are suitably provided in pharmaceutical forms for administration to man and animals.

Thus, the invention, on the other hand, provides pharmaceutical compositions containing one of the products which are the object of the invention in association with pharmaceutical non-toxic excipients.

The choice of the excipient is determined by the pharmaceutical form and by the standard pharmaceutical practice: particularly said formulations can be: tablets, capsules, solutions for oral administration, phials for injection use.

The following examples illustrate, but do not limit, pharmaceutical compositions in accordance with the invention:

| EXAMPLE A: | ingredients contained | mg/capsule |
|---|---|---|
| | N-acetyl-p-phenylalanyl-p-phenylalanine-p-histidineamide | 100 |
| | lactose | 10 |
| EXAMPLE B: | ingredients contained | mg/tablet |
| | N-acetyl-p-phenylalanyl-p-phenylalanine-p-histidine methylester | 150 |
| | starch, lactose, talc | 50 |
| EXAMPLE C: | ingredients contained | mg/drink ampoule |
| | N-acetyl-p-phenylalanyl-d-phenylalanine-p-histidine-methylester.HCl | 200 |
| | sugar | 3000 |
| | aromatizers, H$_2$O q.s. to 10 ml. | |
| EXAMPLE D: | ingredients contained | mg/phial |
| | N-acetyl-p-phenylalanyl-p-phenylalanyl-p-histidineamide hydrochloride | 100 |
| | Distilled H$_2$O q.s. to 2 ml. | |

A great variety of compositions can be made by substituting other excipients to those which are mentioned in this patent. Further, the pharmaceutical compositions of this invention can comprise, in addition to the active element which forms the object of this patent, one or more other therapeutically active substances, compatible with the former and which yield desirable complementary effects.

When the substance of this patent is used in human therapy, a daily dosage from 50 to 400 mg per oral route is generally satisfactory; the exact administration dosage, however, could vary dependently on several factors such as gravity of the symptoms to be treated, age, health and weight of the patient.

We claim:

1. Tripeptides of the general formula:

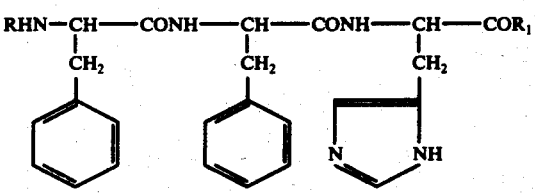

wherein
R = — H, COCH$_3$, alkyl
R$_1$ = —OH, —NH$_2$, —NH alkyl (C$_1$-C$_5$) —O alkyl (C$_1$-C$_5$)
resulting from condensing of racemic, levorotatory and dextrorotatory phenylalanine and histidine.

2. N-acetyl-l-phenylalanyl-d-phenylalanyl-l-histidine methylester.

3. N-acetyl-l-phenylalanyl-d-phenylalanyl-l-histidineamide.

4. N-acetyl-dl-phenylalanyl-dl-phenylalanyl-dl-histidine methylester.
5. N-acetyl-l-phenylalanyl-l-phenylalanyl-l-histidine methylester.
6. N-acetyl-l-phenylalanyl-l-phenylalanyl-l-histidineamide.
7. N-acetyl-l-phenylalanyl-l-phenylalanyl-l-histidine.
8. N-acetyl-l-phenylalanyl-l-phenylalanyl-l-histidylmethylamide.
9. A pharmaceutical composition with anti-ulcer activity, containing, as an active element, 50 to 400 mg of one or more of the tripeptides of claim 1.

* * * * *